US007559958B2

(12) United States Patent
Cottard et al.

(10) Patent No.: US 7,559,958 B2
(45) Date of Patent: Jul. 14, 2009

(54) DYEING COMPOSITION COMPRISING AT LEAST ONE OXIDATION DYE AND AT LEAST ONE AMPHOTERIC POLYMER COMPRISING ACRYLAMIDE, DIALKYLDIALLYLAMMONIUM HALIDE AND A HIGH LEVEL OF VINYLCARBOXYLIC ACID

(75) Inventors: François Cottard, Courbevoie (FR); Gautier Deconinck, Saint-Gratien (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/889,243

(22) Filed: Aug. 10, 2007

(65) Prior Publication Data

US 2008/0034507 A1    Feb. 14, 2008

Related U.S. Application Data

(60) Provisional application No. 60/841,235, filed on Aug. 31, 2006.

(30) Foreign Application Priority Data

Aug. 10, 2006    (FR)    .................................... 06 07247

(51) Int. Cl.
    *A61Q 5/10*    (2006.01)
(52) U.S. Cl. ...................... 8/405; 8/406; 8/409; 8/410; 8/421; 8/435; 8/552; 8/554; 8/555; 8/558
(58) Field of Classification Search ............... 8/405, 8/406, 409, 410, 421, 435, 552, 554, 555, 8/558

See application file for complete search history.

(56) References Cited

U.S. PATENT DOCUMENTS

| | | | |
|---|---|---|---|
| 4,003,699 A | 1/1977 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 2002/0050013 A1 | 5/2002 | Vidal et al. | |
| 2003/0019051 A9 | 1/2003 | Vidal et al. | |
| 2004/0060126 A1* | 4/2004 | Cottard et al. .................. | 8/405 |
| 2004/0133996 A1 | 7/2004 | Wolff et al. | |
| 2005/0015895 A1 | 1/2005 | Azizova et al. | |
| 2008/0066772 A1 | 3/2008 | Cottard et al. | |

FOREIGN PATENT DOCUMENTS

| DE | 23 59 399 A1 | 6/1975 |
|---|---|---|
| DE | 38 43 892 A1 | 6/1990 |
| DE | 41 33 957 A1 | 4/1993 |
| DE | 195 43 988 A1 | 5/1997 |
| EP | 0 521 665 A1 | 1/1993 |
| EP | 0 522 755 A1 | 1/1993 |
| EP | 1 048 290 A2 | 11/2000 |
| FR | 2 586 913 A1 | 3/1987 |
| FR | 2 733 749 A1 | 11/1996 |
| FR | 2 750 048 A1 | 12/1997 |
| FR | 2 817 467 A1 | 6/2002 |
| GB | 1 026 978 | 4/1966 |
| GB | 1 153 196 | 5/1969 |
| JP | 2-19576 | 1/1990 |
| JP | 9-110659 | 4/1997 |
| WO | WO 94/06403 | 3/1994 |
| WO | WO 94/08969 | 4/1994 |
| WO | WO 94/08970 | 4/1994 |
| WO | WO 96/15765 | 5/1996 |
| WO | WO 02/45674 A1 | 6/2002 |

OTHER PUBLICATIONS

STIC Search Report dated Aug. 8, 2008.*
Product Bulletin PC-PolyQ-39.*
French Search Report for FR 0607247, dated Mar. 27, 2007.
English language abstract of JP 2-19576, Jan. 23, 1990.
English language abstract of JP 9-110659, Apr. 28, 1997.
Declaration Under 37 C.F.R. 1.132 executed by G. Deconinck on Jan. 15, 2009, as-filed in co-pending U.S. Appl. No. 11/889,239 on Feb. 13, 2009, 6 pages.
French Search Report issued in FR 06/07244, dated Mar. 13, 2007, cited in co-pending U.S. Appl. No. 11/889,239; 2 pages.

(Continued)

*Primary Examiner*—Eisa B Elhilo
(74) *Attorney, Agent, or Firm*—Finnegsn, Henderson, Farabow, Garrett & Dunner

(57) ABSTRACT

Disclosed herein is a composition for the oxidation dyeing of keratinous fibers, for example, human keratinous fibers, such as the hair, comprising, in a medium appropriate for dyeing, at least one oxidation dye and at least one polymer comprising the repetition of: (i) at least one unit derived from a monomer of acrylamide type, (ii) at least one unit derived from a monomer of dialkyldiallylammonium halide type, and (iii) at least 50 mol % of at least one unit derived from a monomer of vinylcarboxylic acid type. The composition disclosed is easily and rapidly removed during the rinsing stage while retaining good rheological and dyeing properties.

22 Claims, No Drawings

OTHER PUBLICATIONS

Aug. 13, 2008 Office Action issued in co-pending U.S. Appl. No. 11/889,239; 8 pages.

Response to Aug. 13, 2008 Office Action as-filed in co-pending U.S. Appl. No. 11/889,239 on Feb. 13, 2009; 5 pages.

* cited by examiner

DYEING COMPOSITION COMPRISING AT LEAST ONE OXIDATION DYE AND AT LEAST ONE AMPHOTERIC POLYMER COMPRISING ACRYLAMIDE, DIALKYLDIALLYLAMMONIUM HALIDE AND A HIGH LEVEL OF VINYLCARBOXYLIC ACID

This application claims benefit of U.S. Provisional Application No. 60/841,235, filed Aug. 31, 2006, the contents of which are incorporated herein by reference. This application also claims benefit of priority under 35 U.S.C. § 119 to French Patent Application No. FR 06/07247, filed Aug. 10, 2006, the contents of which are also incorporated herein by reference.

Disclosed herein is a composition for the oxidation dyeing of keratinous fibers, for example, human keratinous fibers, such as the hair, comprising, in a medium appropriate for dyeing, at least one oxidation dye and at least one specific amphoteric polymer described below.

It is known to dye keratinous fibers such as human hair with dyeing compositions comprising oxidation dyes, such as oxidation dye precursors and coloring modifiers.

Oxidation dye precursors, generally known as oxidation bases, are initially colorless or weakly colored compounds which, in combination with oxidizing products, can give rise, by an oxidative coupling process, to colored and coloring compounds. These may be, for example, compounds such as ortho- or para-phenylenediamines, ortho- or para-aminophenols and heterocyclic bases.

It is also known that it is possible to vary the shades obtained with these oxidation bases by combining them with couplers or coloring modifiers, the latter may be chosen from, for example, meta-diaminobenzenes, meta-aminophenols, meta-diphenols and certain heterocyclic compounds, such as indole compounds.

The variety of the molecules involved as oxidation bases and couplers makes it possible to obtain a rich pallet of colors.

The "permanent" coloring obtained by virtue of these oxidation dyes, also known as oxidation coloring, furthermore has to satisfy a certain number of criteria. For example, it must not be toxic, it should make it possible to obtain shades with the desired intensity, and it should behave well in the face of external agents, such as light, bad weather, washing, permanent waving, perspiration and rubbing.

The dyes should also make it possible to cover white hair and, finally, be as nonselective as possible, that is to say make it possible to obtain the smallest possible differences in coloring along the same keratinous fiber, which may be differently sensitized (that is to say, damaged) between its tip and its root.

European Patent Application EP 1 048 290 describes a composition for the oxidation dyeing of the hair comprising an oxidation dye precursor, a coupler and an amphoteric polymer comprising repeat units (a) of acrylic acid and (b) of a cationic monomer chosen from methacrylamidopropyltrimethylammonium chloride, dimethyldiallylammonium chloride and their mixtures, the molar ratio of the units (a) to the units (b) being greater than or equal to ⅓. This composition can make it possible to improve the deposition of the dyes on the hairs and thus to render the dye more effective.

United States Patent Application Publication No. 2005/0015895 describes a composition for the oxidation dyeing of the hair comprising an oxidation dye and a quaternary amphoteric terpolymer comprising the following repeat units: (a) methacrylamidopropyltrimethylammonium chloride or dimethyldiallylammonium chloride (b) acrylic acid or sodium methacrylate, and (c) acrylamide, with an (a)/(b) ratio of greater than or equal to 4. This composition can make it possible to obtain a better conditioning effect on hair fibers.

Finally, French Patent No. FR 2 817 467 describes a composition for the oxidation dyeing of keratinous fibers comprising an oxidation dye, an associative polymer and a polymer comprising units derived from a monomer of (i) acrylamide, (ii) dialkyldiallylammonium halide and (iii) vinylcarboxylic acid type. This composition can make it possible to obtain an optimum application to the fibers, for example it can form a composition that does not run, without, however, detrimentally affecting the qualities of the coloring.

However, the oxidation dyeing compositions of the prior art are often difficult to employ. For instance, after a more or less lengthy leave-in time, the composition applied to the hair has to be removed by rinsing and this rinsing stage is often lengthy and difficult, the product being difficult to remove.

Accordingly, there is a need in the art for novel compositions for the oxidation dyeing of keratinous fibers, which do not exhibit the disadvantages of the prior art. Thus, the present disclosure relates to dyeing compositions which are easier and faster to remove but which nevertheless remain easy to apply (for example, which do not run, and remain highly localized at the point of application), without, however, detrimentally affecting the strength, the chromaticity, and the selectivity of the coloring.

Disclosed herein is a composition for the oxidation dyeing of keratinous fibers, for example, human keratinous fibers, such as the hair, comprising, in a medium appropriate for dyeing, at least one oxidation dye and at least one amphoteric polymer comprising the repetition of:

(i) at least one unit derived from a monomer of acrylamide type, (ii) at least one unit derived from a monomer of dialkyldiallylammonium halide type, and (iii) at least 50 mol % of at least one units derived from a monomer of vinylcarboxylic acid type.

The composition disclosed herein can be easily and rapidly removed during the rinsing stage while retaining good rheological properties. In addition, it can make it possible to improve the cosmetic properties of the hair, such as disentangling and smoothing.

Finally, the dyeing properties of this composition can be highly satisfactory, both as regards the selectivity and the intensity of the coloring obtained.

The present disclosure further relates to a method for dyeing keratinous fibers employing the composition disclosed herein.

The present disclosure also relates to a multicompartment device for the implementation of the method disclosed herein.

The present disclosure further relates to the use, for the oxidation dyeing of keratinous fibers, of the composition as disclosed herein.

Finally, the present disclosure relates to the use, in an oxidation dyeing composition, of an amphoteric polymer as described herein for bringing about easy and rapid removal of the composition during the rinsing stage.

Unless otherwise indicated, the limits of the ranges of values which are given in the context of the present disclosure are included in these ranges.

According to at least one embodiment, the units derived from a monomer of acrylamide type of the amphoteric polymer of use of the present disclosure are units with the following structure (I):

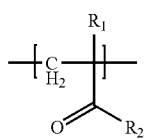
(I)

in which:
R$_1$ is H or CH$_3$, and
R$_2$ is chosen from amino, dimethylamino, tert-butylamino, dodecylamino and —NH—CH$_2$OH radicals.

According to at least one embodiment, the amphoteric polymer disclosed herein comprises a single unit of formula (I).

According to at least one embodiment of the present disclosure, the unit derived from a monomer of acrylamide type of formula (I) in which R$_1$ denotes H and R$_2$ is an amino radical, i.e., corresponding to the acrylamide monomer, can be used.

According to at least one embodiment of the present disclosure, the at least one unit derived from a monomer of dialkyldiallylammonium halide type of the amphoteric polymer can be chosen from those of formula (II):

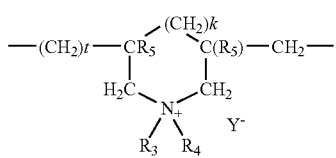
(II)

in which:
k and t are equal to 0 or 1, the sum k+t being equal to 1;
R$_5$ is H or CH$_3$;
R$_3$ and R$_4$ are chosen from, independently of one another, C$_1$-C$_4$ alkyl groups, hydroxy(C$_1$-C$_5$)alkyl groups, and amido(C$_1$-C$_4$)alkyl groups, or R$_3$ and R$_4$ may form, together with the nitrogen atom to which they are attached, heterocyclic groups, such as piperidinyl or morpholinyl; for example, R$_3$ and R$_4$ can be chosen from, independently of one another, C$_1$-C$_4$ alkyl groups;
Y$^-$ is chosen from anions, such as a bromide, chloride, acetate, borate, citrate, tartrate, bisulphate, bisulphite, sulphate and phosphate.

According to at least one embodiment of the present disclosure, units derived from a monomer of dialkyldiallylammonium halide type, include those for which R$_5$ is H and R$_3$ and R$_4$ denote a methyl radical, Y$^-$ denoting a chloride anion.

According to at least one embodiment of the present disclosure, the at least one unit derived from a monomer of vinylcarboxylic acid type of the amphoteric polymer can be chosen from the units of formula (III):

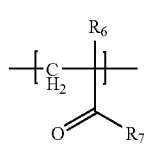
(III)

in which:
R$_6$ is H or CH$_3$,
R$_7$ is a hydroxyl radical or an —NH—C(CH$_3$)$_2$—CH$_2$—SO$_3$H radical.

For example, the at least one unit derived from a monomer of vinylcarboxylic acid type may be chosen from acrylic acid, methacrylic acid and 2-acrylamido-2-methylpropanesulfonic acid monomers.

According to at least one embodiment of the present disclosure, the at least one unit derived from a monomer of vinylcarboxylic acid type can be acrylic acid, for which R$_6$ denotes a hydrogen atom and R$_7$ denotes a hydroxyl radical.

As disclosed herein, the at least one amphoteric polymer comprise at least 50 mol % of units derived from a monomer of vinylcarboxylic acid type.

At least according to one embodiment of the present disclosure, they comprise from 50 to 90 mol % of units derived from a monomer of vinylcarboxylic acid type, for example, from 50 to 75 mol %.

The contents of the other two units may be as follows:
from 1 to 40 mol %, for example, from 5 to 25 mol %, of units derived from a monomer of acrylamide type;
from 1 to 40 mol %, for example, from 5 to 25 mol %, of units derived from a monomer of dialkyldiallylammonium halide type.

The at least one amphoteric polymer used according to the present disclosure may also comprise additional units, other than the units derived from monomers of acrylamide, dialkyldiallylammonium halide and vinylcarboxylic acid type, provided that they comprise at least 50 mol % of units derived from a monomer of vinylcarboxylic acid type.

Non-limiting mention may be made, as example of polymers comprising units derived from monomers of (i) acrylamide, (ii) dialkyldiallylammonium halide and (iii) vinylcarboxylic acid type, of acrylamide/dimethyldiallylammonium chloride/acrylic acid terpolymers, listed in the CTFA Dictionary, International Cosmetic Ingredient Dictionary, 10th Edition, 2004, under the name "Polyquaternium 39." The polymers according to the present disclosure may thus be chosen from the Polyquaterniums 39 comprising at least 50 mol % of acrylic acid, such as, for example, the product sold under the name Merquat 3333 by Nalco.

The amphoteric polymer according to the present disclosure can be prepared conventionally by polymerization starting from its various monomers according to techniques known to a person skilled in the art, such as, radical polymerization.

The at least one amphoteric polymer used in the context of the present disclosure can be, according to at least one embodiment, present in an amount ranging from 0.1 to 10% by weight, such as, from 0.5 to 5% by weight, with respect to the total weight of the dyeing composition. For example, the at least one amphoteric polymer disclosed herein can be present in an amount ranging from 1 to 4% by weight, with respect to the total weight of the dyeing composition.

The composition disclosed herein comprises at least one oxidation dye which can be chosen from oxidation bases and couplers.

The oxidation bases which can be used in the context of the present disclosure are chosen from those known conventionally in oxidation dyeing, such as, ortho- and para-phenylenediamines, double bases, ortho- and para-aminophenols, heterocyclic bases and the acid addition salts thereof.

The para-phenylenediamines which can be used in the context of the present disclosure may be chosen, by way of non-limiting example, from the compounds of formula (IV) and the acid addition salts thereof:

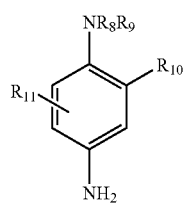

in which:

R$_8$ is chosen from hydrogen, C$_1$-C$_4$ alkyl radicals, C$_1$-C$_4$ monohydroxyalkyl radicals, C$_2$-C$_4$ polyhydroxyalkyl radicals, (C$_1$-C$_4$)alkoxy(C$_1$-C$_4$)alkyl radicals, C$_1$-C$_4$ alkyl radicals substituted by a nitrogenous group, a phenyl radical and a 4'-aminophenyl radical;

R$_9$ is chosen from hydrogen, C$_1$-C$_4$ alkyl radicals, C$_1$-C$_4$ monohydroxyalkyl radicals, C$_2$-C$_4$ polyhydroxyalkyl radicals, (C$_1$-C$_4$)alkoxy(C$_1$-C$_4$)alkyl radicals or C$_1$-C$_4$ radicals substituted by a nitrogenous group;

R$_8$ and R$_9$ can also form, with the nitrogen atom which carries them, a 5- or 6-membered nitrogenous heterocycle optionally substituted by at least one entity chosen from alkyl, hydroxyl and ureido groups;

R$_{10}$ is chosen from hydrogen, halogens, such as chlorine, C$_1$-C$_4$ alkyl radicals, a sulpho radical, a carboxyl radical, C$_1$-C$_4$ monohydroxyalkyl radicals, C$_1$-C$_4$ hydroxyalkoxy radicals, C$_1$-C$_4$ acetylaminoalkoxy radicals, C$_1$-C$_4$ mesylaminoalkoxy radicals and C$_1$-C$_4$ carbamoylaminoalkoxy radicals;

R$_{11}$ is chosen from hydrogen, halogens and C$_1$-C$_4$ alkyl radicals.

Non-limiting mention may be made, among the nitrogenous groups of the above formula (IV), of the amino, mono (C$_1$-C$_4$)alkylamino, di(C$_1$-C$_4$)alkylamino, tri(C$_1$-C$_4$)alkylamino, monohydroxy(C$_1$-C$_4$)alkylamino, imidazolinium and ammonium radicals.

Non-limiting mention may be made, for example, among the para-phenylenediamines of above formula (IV), of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine and the acid addition salts thereof.

Non-limiting mention may be made, for instance, among the para-phenylenediamines of above formula (IV), to para-phenylenediamine, para-toluoylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and the acid addition salts thereof.

According to the disclosure, "double bases" is understood to mean the compounds comprising at least two aromatic nuclei on which are carried amino and/or hydroxyl groups.

Non-limiting mention may be made, among the double bases which can be used as oxidation bases in the composition as disclosed herein, of compounds of formula (V) and the acid addition salts thereof:

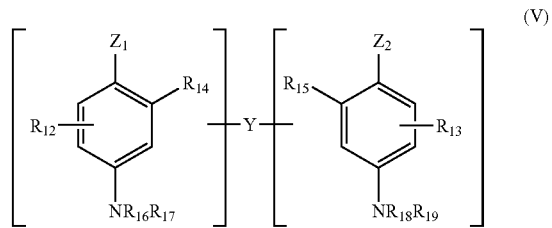

in which:

Z$_1$ and Z$_2$, which are identical or different, can be a hydroxyl or —NH$_2$ radical which can be substituted by a C$_1$-C$_4$ alkyl radical or by a connecting arm Y;

the connecting arm Y is a linear or branched C$_1$-C$_{14}$ alkylene chain which may be interrupted or terminated by at least one nitrogenous group and/or by at least one heteroatom, such as oxygen, sulphur or nitrogen atoms, and which is optionally substituted by at least one entity chosen from hydroxyl and C$_1$-C$_6$ alkoxy radicals;

R$_{12}$ and R$_{13}$ are chosen from hydrogen and halogen atoms, C$_1$-C$_4$ alkyl radicals, C$_1$-C$_4$ monohydroxyalkyl radicals, C$_2$-C$_4$ polyhydroxyalkyl radicals, C$_1$-C$_4$ aminoalkyl radicals and a connecting arm Y;

R$_{14}$, R$_{15}$, R$_{16}$, R$_{17}$, R$_{18}$ and R$_{19}$, which are identical or different, can be chosen from hydrogen, a connecting arm Y and C$_1$-C$_4$ alkyl radicals;

wherein the compounds of formula (V) only comprise a single connecting arm Y per molecule.

Non-limiting mention may be made, for example, among the nitrogenous groups of the above formula (V); of the amino, mono(C$_1$-C$_4$)alkylamino, di(C$_1$-C$_4$)alkylamino, tri (C$_1$-C$_4$)alkylamino, monohydroxy(C$_1$-C$_4$)alkylamino, imidazolinium and ammonium radicals.

Non-limiting mention may be made, for instance, among the double bases of above formula (V), of N,N'-bis(β-hydroxyethyl)-N,N'-bis(4'-aminophenyl)-1,3-diamino-propanol, N,N'-bis(β-hydroxyethyl)-N,N'-bis(4'-aminophenyl) ethylenediamine, N,N'-bis(4-aminophenyl)-tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diamino-phenoxy)-3,5-dioxaoctane and the acid addition salts thereof.

In at least one embodiment of the present disclosure, N,N'-Bis(β-hydroxyethyl)-N,N'-bis(4'-aminophenyl)-1,3-diaminopropanol, 1,8-bis(2,5-diaminophenoxy)-3,5-dioxaoctane or the acid addition salts thereof are chosen as double bases of formula (V).

In at least one embodiment of the present disclosure, the para-aminophenols may be chosen from the compounds of formula (VI) and the acid addition salts thereof:

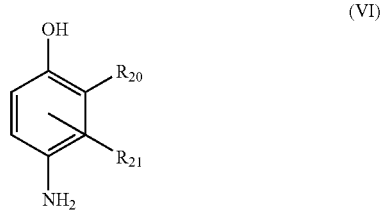

(VI)

in which:
R$_{20}$ is chosen from hydrogen, halogens, such as fluorine, C$_1$-C$_4$ alkyl radicals, C$_1$-C$_4$ monohydroxyalkyl radicals, (C$_1$-C$_4$)alkoxy(C$_1$-C$_4$) alkyl radicals, C$_1$-C$_4$ aminoalkyl radicals and hydroxy(C$_1$-C$_4$)alkylamino-(C$_1$-C$_4$)alkyl radicals, R$_{21}$ is chosen from hydrogen, halogens, such as fluorine, C$_1$-C$_4$ alkyl radicals, C$_1$-C$_4$ monohydroxyalkyl radicals, C$_2$-C$_4$ polyhydroxyalkyl radicals, C$_1$-C$_4$ aminoalkyl radicals, C$_1$-C$_4$ cyanoalkyl radicals and (C$_1$-C$_4$)alkoxy (C$_1$-C$_4$)alkyl radicals.

Non-limiting mention may be made, among the para-aminophenols of formula (VI), of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl) phenol, 4-amino-2-(aminomethyl)-phenol, 4-amino-2-[(β-hydroxyethyl)aminomethyl]phenol and the acid addition salts thereof.

In at least one embodiment, the ortho-aminophenols which may be used as oxidation bases in the context of the present disclosure include 2-aminophenol, 2-amino-1-hydroxy-5-methylbenzene, 2-amino-1-hydroxy-6-methylbenzene, 5-acetamido-2-aminophenol and the acid addition salts thereof.

Non-limiting mention may also be made, among the heterocyclic bases which can be used as oxidation bases in the composition disclosed herein, of pyridine derivatives, pyrimidine derivatives, pyrazole derivatives and the acid addition salts thereof.

Non-limiting mention may further be made, among pyridine derivatives, of the compounds disclosed, for example, in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diamino-pyridine and the acid addition salts thereof.

Non-limiting mention may be made, among pyrimidine derivatives, of the compounds disclosed, for example, in German Patent DE 2 359 399 or Japanese Patent Nos. JP 88-169 571 and JP 91-10659 or Patent Application WO 96/15765, such as 2,4,5,6-tetraminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a] pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo [1,5-a]pyrimidine-3,7-diamine; 2,6-dimethylpyrazolo[1,5-a] pyrimidine-3,7-diamine; 2,5,N7,N7-tetramethylpyrazolo[1, 5-a]pyrimidine-3,7-diamine; 3-amino-5-methyl-7-(imidazolylpropylamino)pyrazolo[1,5-a]pyrimidine; their tautomeric forms, when there exists a tautomeric equilibrium, and the acid addition salts thereof.

Non-limiting mention may be made, among pyrazole derivatives, of the compounds disclosed in German Patent Nos. DE 3 843 892 and DE 4 133 957, and in the Patent Applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chloro-benzyl) pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino) pyrazole, 3,5-diamino-4-(β-hydroxyethyl)amino-1-methylpyrazole and the acid addition salts thereof.

The composition disclosed herein comprises a total amount of oxidation base(s) ranging from 0.0005 to 12% by weight, with respect to the total weight of the composition. In at least one embodiment, it comprises a total amount of oxidation base(s) ranging from 0.005 to 8% by weight and, for example, from 0.05 to 5% by weight, with respect to the total weight of the composition.

The at least one coupler that may be used in the composition disclosed herein can be chosen from those conventionally used in oxidation dyeing compositions, such as meta-aminophenols, meta-phenylenediamines, meta-diphenols, naphthols and heterocyclic couplers, such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and the acid addition salts thereof.

The at least one coupler may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c][1,2,4]triazole, 2,6-dimethylpyrazolo[1,5-b][1,2,4]triazole and the acid addition salts thereof.

The composition according to the present disclosure can comprise a total amount of coupler(s) ranging from 0.0001 to 15% by weight, with respect to the total weight of the composition. For instance, it can comprise a total amount of coupler(s) ranging from 0.001 to 10% by weight, such as from 0.01 to 8% by weight, with respect to the total weight of the composition.

The acid addition salts of the oxidation bases and of the couplers may be chosen, for instance, from hydrochlorides, hydrobromides, sulphates and tartrates, lactates and acetates.

According to at least one embodiment of the present disclosure, the composition comprises at least one oxidation base and at least one coupler.

The dyeing composition disclosed herein may additionally comprise at least one direct dye which can be chosen, for example, from nitrobenzene dyes, azo direct dyes or methine direct dyes. These direct dyes can be of nonionic, anionic or cationic nature.

The composition disclosed herein may further comprise at least one oxidizing agent.

Such an oxidizing agent can be chosen, for instance, from hydrogen peroxide, urea peroxide, alkali metal bromates, alkali metal ferricyanides, and persalts, such as perborates and persulphates.

In at least one embodiment, the at least one oxidizing agent is hydrogen peroxide. This oxidizing agent can be in an oxidizing composition, for example composed of an aqueous hydrogen peroxide solution, the content of which can vary, for instance, from about 1 to 40 volumes, for example, from about 5 to 40 volumes.

Non-limiting use may also be made, as oxidizing agent, of at least one oxidation-reduction enzyme, such as laccases, peroxidases and 2-electron oxidoreductases (such as uricase). Such enzymes may also be used in the presence of their respective donors or cofactors.

The medium appropriate for dyeing, also referred to as dyeing vehicle, is a cosmetic medium composed of, for instance, water or of a mixture of water and of at least one cosmetically acceptable organic solvent. Non-limiting mention may be made, as examples of organic solvents, of alcohols, such as ethyl alcohol, isopropyl alcohol, benzyl alcohol and phenylethyl alcohol, or glycols or glycol ethers, such as, for example, ethylene glycol monomethyl, monoethyl and monobutyl ethers, propylene glycol and its ethers, such as, for example, propylene glycol monomethyl ether, butylene glycol, dipropylene glycol, and also diethylene glycol alkyl ethers, such as, for example, diethylene glycol monoethyl ether or monobutyl ether. The solvents can be present in concentrations ranging from approximately 0.5 to 20% by weight, for example, ranging from approximately 2 to 10% by weight, with respect to the total weight of the composition.

The composition disclosed herein may also include at least one adjuvant chosen from the various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, other than the amphoteric polymers according to the invention, inorganic or organic thickening agents, such as anionic, cationic, nonionic and amphoteric polymeric associative thickeners, antioxidizing agents, penetration agents, sequestering agents, fragrances, buffers, dispersing agents, conditioning agents, such as, for example, volatile or nonvolatile and modified or unmodified silicones, film-forming agents, ceramides, preserving agents or opacifying agents.

The above adjuvants may be present in an amount, for each adjuvant, ranging from 0.01 to 20% by weight, with respect to the weight of the dyeing composition.

Of course, a person skilled in the art will take care to choose the optional additional compound or compounds mentioned above so that the beneficial properties intrinsically attached to the compositions according to the present disclosure are not, or not substantially, detrimentally affected by the envisaged addition or additions.

The pH of the composition in accordance with the present disclosure ranges from 3 to 12, for example, from 5 to 11. It can be adjusted to the desired value using acidifying or basifying agents commonly used in the dyeing of keratinous fibers or alternatively using conventional buffering systems.

Non-limiting mention may be made, among basifying agents, by way of example, of aqueous ammonia, alkaline carbonates, alkanolamines, such as mono-, di- and triethanolamines, and their derivatives, hydroxyalkylamines and ethylenediamines which are oxyethylenated and/or oxypropylenated, sodium hydroxide, potassium hydroxide and the compounds of formula (VII):

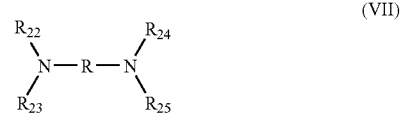

(VII)

in which R is a propylene residue optionally substituted by a hydroxyl group or a $C_1$-$C_4$ alkyl radical and $R_{22}$, $R_{23}$, $R_{24}$ and $R_{25}$, which are identical or different, may be chosen from hydrogen, $C_1$-$C_4$ alkyl radicals and $C_1$-$C_4$ hydroxyalkyl radicals.

Non-limiting mention may be made, among acidifying agents, by way of example, of inorganic or organic acids, such as hydrochloric acid, orthophosphoric acid, carboxylic acids, such as tartaric acid, citric acid or lactic acid, or sulphonic acids.

The dyeing composition according to the present disclosure can be provided in various forms, such as in the form of liquids, creams or gels, or in any other form appropriate for carrying out dyeing of keratinous fibers, such as human hair.

The method of the present disclosure relates to the application of the composition as defined above to the fibers and the color is developed using an oxidizing agent. The color can be developed at acidic, neutral or alkaline pH. For instance, in one embodiment, the coloring is developed at neutral pH. The oxidizing agent can be added to the composition of the present disclosure either at the time of use or it can be employed starting from an oxidizing composition comprising it, applied simultaneously with or sequentially to the composition as disclosed herein.

According to at least one embodiment, the composition disclosed herein is mixed, for instance, at the time of use, with a composition comprising, in a medium appropriate for dyeing, at least one oxidizing agent, this oxidizing agent being present in an amount sufficient to develop a coloring. The mixture obtained is subsequently applied to the keratinous fibers. After a leave-in time generally varying from about 1 to 60 minutes, such as from about 5 to 45 minutes, the keratinous fibers are rinsed, washed with a shampoo, rinsed again and then dried.

The present disclosure further relates to a dyeing kit or multicompartment device in which at least one first compartment includes the dyeing composition as disclosed herein, with the exception of the oxidizing agent, and at least one second compartment includes an oxidizing composition comprising at least one oxidizing agent. This device can be equipped with an applicator for allowing the desired mixture to be deposited on the hair, such as the devices described in French Patent No. FR-2 586 913.

The present disclosure further relates to the use, for the oxidation dyeing of keratinous fibers, for example, human keratinous fibers, such as the hair, of a dyeing composition as defined above.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

In these examples, all the amounts are shown as percent by weight of active material (A.M.), with respect to the total weight of the composition, unless otherwise indicated. Notwithstanding that the numerical ranges and parameters setting forth the broad scope of the present disclosure are approximations, the numerical values set forth in the specific example are reported as precisely as possible. Any numerical values, however, inherently contain certain errors necessarily resulting from the standard deviation found in their respective testing measurements.

The following examples are intended to illustrate the present disclosure in a non-limiting manner.

EXAMPLES

Two dyeing compositions were prepared starting from the following compounds (comparative composition A, composition B according to the invention):

| Component | Composition A (comparative) | Composition B (inventive) |
|---|---|---|
| Oxyethylenated lauryl alcohol comprising 12 EO, sold under the name Rewopal 12 by Goldschmidt | 7.5 | 7.5 |
| Glycol monostearate | 2 | 2 |
| Oxyethylenated oleocetyl alcohol comprising 30 EO, sold under the name Emulgin O 30 by Cognis | 3 | 3 |
| Oxyethylenated decyl alcohol comprising 3 EO, sold under the name Emulgin BL 309 by Cognis | 10 | 10 |
| Cetearyl alcohol ($C_{16}/C_{18}$: 50/50), sold under the name Lanette O OR by Cognis | 10 | 10 |
| Natural lauric acid | 2.5 | 2.5 |
| Hydrophobic pyrogenic silica, sold under the name Aerosil R972 by Degussa | 1 | 1 |
| Crosslinked polyacrylic acid, sold under the name Carbopol 980 by Noveon | 0.4 | 0.4 |
| Propylene glycol | 10 | 10 |
| Monoethanolamine | 1.2 | 1.2 |
| Acrylamide/diallyldimethylammonium chloride/acrylic acid polymer (Merquat 3333 from Nalco) | — | 2.4 |
| Diethylenetriaminepentaacetic acid, pentasodium salt, as a 40% aqueous solution, sold under the name Dissolvine D40 by Akzo Nobel | 2 | 2 |

-continued

| Component | Composition A (comparative) | Composition B (inventive) |
|---|---|---|
| Ammonium thiolactate, as a 58% aqueous solution (50% of thiolactic acid) | 0.8 | 0.8 |
| Ascorbic acid | 0.2 | 0.2 |
| Titanium dioxide | 0.2 | 0.2 |
| Aqueous ammonia comprising 20% of $NH_3$ | 10 | 10 |
| 2-Methyl-5-(hydroxyethyl)aminophenol | 0.86 | 0.86 |
| p-Aminophenol | 0.41 | 0.41 |
| 4-Amino-2-hydroxytoluene | 0.57 | 0.57 |
| 6-Hydroxyindole | 0.068 | 0.068 |
| p-Phenylenediamine | 0.49 | 0.49 |
| Resorcinol | 0.1 | 0.1 |
| Fragrance | q.s. | q.s. |
| Water | q.s. for 100 | q.s. for 100 |

Each of the compositions A and B was mixed, in a 1+1.5 ratio by weight, with an oxidizing composition having a hydrogen peroxide content of 20 volumes.

The pH values of the mixtures thus obtained was 10.

These mixtures were applied to grey hair comprising 90% of white hairs for a leave-in time of 30 minutes at ambient temperature.

The hair was subsequently rinsed, washed with standard shampoo, then rinsed with water and dried.

Using the two compositions as disclose above, a shade with an attractive coppery red highlight possessing good persistence was obtained in the two cases.

It was observed that the composition resulting from the mixture of inventive composition B with the oxidizing composition was more easily rinsed than that obtained with comparative composition A.

In addition, after coloring with inventive composition B, it was observed that the hair was particularly smooth.

What is claimed is:

1. A composition for the oxidation dyeing of keratinous fibers comprising, in a medium appropriate for dyeing, at least one oxidation dye and at least one amphoteric polymer comprising a repetition of:
   (i) at least one unit derived from a monomer of acrylamide type,
   (ii) at least one unit derived from a monomer of dialkyldiallylammonium halide type, and
   (iii) at least 50 mol % of at least one unit derived from a monomer of vinylcarboxylic acid type.

2. The composition according to claim 1, wherein the at least one unit derived from a monomer of acrylamide type is chosen from units of formula (I):

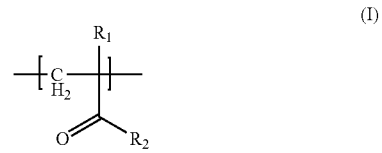

in which:
   $R_1$ is H or $CH_3$,
   $R_2$ is chosen from amino, dimethylamino, tert-butylamino, dodecylamino and —NH—$CH_2OH$ radicals.

3. The composition according to claim 2, wherein $R_1$ is H and $R_2$ is an amino radical.

4. The composition according to claim 1, wherein the at least one unit derived from a monomer of dialkyldiallylammonium halide type is chosen from units of formula (II):

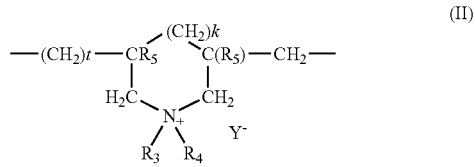

in which:
k and t are equal to 0 or 1, the sum k+t being equal to 1;
$R_5$ is H or $CH_3$;
$R_3$ and $R_4$ are chosen from, independently of one another, $C_1$-$C_4$ alkyl groups, hydroxy($C_1$-$C_5$)alkyl groups, and amido($C_1$-$C_4$)alkyl groups, or $R_3$ and $R_4$ may form, jointly with the nitrogen atom to which they are attached, heterocyclic groups;
$Y^-$ is a bromide, chloride, acetate, borate, citrate, tartrate, bisulphate, bisulphite, sulphate or phosphate anion.

5. The composition according to claim 4, wherein $R_5$ is hydrogen, $R_3$ and $R_4$ are methyl radicals, and $Y^-$ is a chloride anion.

6. The composition according to claim 1, wherein the at least one unit derived from a monomer of vinylcarboxylic acid type is chosen from the units of formula (III):

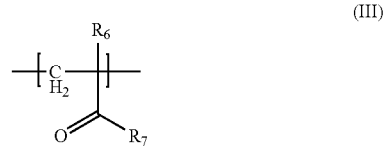

in which:
$R_6$ is H or $CH_3$,
$R_7$ is a hydroxyl radical or an —NH—C($CH_3$)$_2$—$CH_2$—$SO_3H$ radical.

7. The composition according to claim 6, wherein $R_6$ is hydrogen and $R_7$ is a hydroxyl radical.

8. The composition according to claim 1, wherein the at least one amphoteric polymer comprises from 50 to 90 mol % of at least one unit derived from a monomer of vinylcarboxylic acid type.

9. The composition according to claim 1, wherein the at least one amphoteric polymer comprises from 1 to 40 mol % of at least one unit derived from a monomer of acrylamide type.

10. The composition according to claim 1, wherein the at least one amphoteric polymer comprises from 1 to 40 mol % of at least one unit derived from a monomer of dialkyldiallylammonium halide type.

11. The composition according to claim 1, wherein the at least one amphoteric polymer is chosen from acrylamide/dimethyldiallylammonium chloride/acrylic acid terpolymers comprising at least 50 mol % of acrylic acid.

12. The composition according to claim 1, wherein the at least one amphoteric polymer is present in an amount ranging from 0.1 to 10% by weight, with respect to the total weight of the dyeing composition.

13. The composition according to claim 1, wherein the at least one oxidation dye is chosen from oxidation bases and couplers.

14. The composition according to claim 13, wherein the at least one oxidation base is chosen from ortho- and para-phenylenediamines, double bases, ortho- and para-aminophenols, heterocyclic bases and the acid addition salts thereof.

15. The composition according to claim 13, wherein the total amount of oxidation base present in the composition ranges from 0.0005 to 12% by weight, with respect to the total weight of the composition.

16. The composition according to claim 13, wherein the at least one coupler is chosen from meta-aminophenols, meta-phenylenediamines, meta-diphenols, naphthols, heterocyclic couplers and the acid addition salts thereof.

17. The composition according to claim 13, wherein the total amount of coupler present in the composition ranges from 0.0001 to 15% by weight, with respect to the total weight of the composition.

18. The composition according to claim 1, further comprising at least one oxidizing agent.

19. The composition according to claim 18, wherein the at least one oxidizing agent is chosen from hydrogen peroxide, urea peroxide, alkali metal bromates, alkali metal ferricyanides, persalts and oxidation-reduction enzymes optionally with their respective donor or cofactor.

20. A method for dyeing keratinous fibers, comprising
applying to the hair a composition for the oxidation dyeing of keratinous fibers comprising, in a medium appropriate for dyeing, at least one oxidation dye and at least one amphoteric polymer comprising a repetition of:
(i) at least one unit derived from a monomer of acrylamide type,
(ii) at least one unit derived from a monomer of dialkyldiallylammonium halide type, and
(iii) at least 50 mol % of at least one unit derived from a monomer of vinylcarboxylic acid type,
wherein the composition is applied in the presence of at least one oxidizing agent; and
leaving the composition on the keratinous fibers for a time sufficient to develop the desired coloring.

21. A multicompartment device, comprising
at least one first compartment comprising a composition for the oxidation dyeing of keratinous fibers comprising, in a medium appropriate for dyeing, at least one oxidation dye and at least one amphoteric polymer comprising a repetition of:
(i) at least one unit derived from a monomer of acrylamide type,
(ii) at least one unit derived from a monomer of dialkyldiallylammonium halide type, and
(iii) at least 50 mol % of at least one unit derived from a monomer of vinylcarboxylic acid type; and
at least one second compartment comprising at least one oxidizing agent.

22. A method for preparing a quick rinsing dye composition comprising combining, in a medium appropriate for dyeing, at least one oxidation dye and at least one amphoteric polymer comprising a repetition of:
(i) at least one unit derived from a monomer of acrylamide type,
(ii) at least one unit derived from a monomer of dialkyldiallylammonium halide type, and
(iii) at least 50 mol % of at least one unit derived from a monomer of vinylcarboxylic acid type.

* * * * *